United States Patent [19]
Zenhausern

[11] Patent Number: 5,788,853
[45] Date of Patent: Aug. 4, 1998

[54] SUBSTRATE AND METHOD FOR MICROSCOPICAL OBSERVATION OF AMORPHOUS SPECIMENS

[75] Inventor: Frederic Zenhausern, Mohegan Lake, N.Y.

[73] Assignee: International Business Machines Corporation, Armonk, N.Y.

[21] Appl. No.: 609,024

[22] Filed: Feb. 29, 1996

[51] Int. Cl.$^6$ ........................................ B44C 1/22
[52] U.S. Cl. .......................... 216/2; 216/41; 216/56; 216/60; 216/85
[58] Field of Search .................... 216/2, 41, 59, 216/56, 60, 84, 85; 156/626.1, 643.1, 659.11, 661.11, 644.1

[56] References Cited

U.S. PATENT DOCUMENTS

| | | |
|---|---|---|
| 4,919,749 | 4/1990 | Mauger et al. |
| 5,122,663 | 6/1992 | Chang et al. |

OTHER PUBLICATIONS

J. Dubochet et al. "Low Temperature Electron Microscopy", Ann. Rev. Bioeng. 1981, vol. 10, pp.133–149.

W. Chiu. "Electron Microscopy of Frozen, Hydrated Biological Specimens", Ann. Rev. Biophys. Chem. 1986, vol. 15, pp. 237–257.

M. Adrian et al. "Cryo–electron microscopy of viruses", Nature, vol. 308, Mar. 1, 1983, pp. 32–36.

A. Fukami et al. "Micro Grid Techniques (continued) and Their Contribution to Specimen Preparation Techniques for High Resolution Work", Journal of Electron Microscopy, vol. 21, No. 2, 99–108, 1972.

Ximen J. et al. "Three dimensional algebraic reconstruction from three mutually orthogonal projections", Optik 71, No. 4 (1985), pp. 145–148.

T. Sumomogi et al. "Nanoscale layer removal of metal surfaces by scanning probe microscope scratching", J. Vac. Sci. Technol. B., vol. 13, No. 3, May/Jun. 1995, pp. 1257–1260.

S. Hosaka et al. "Fabrication of nanostructures using scanning probe microscopes", J. Vac. Sci. Technol. B 13(6), Nov./Dec. 1995, pp. 2813–2818.

S. C. Minne et al. "Atomic force microscope lithograph using amorphous silicon as a resist and advances in parallel operation", J. Vac. Sci. Technol. B 13(3), May/Jun. 1995, pp. 1380–1385.

R.J. Jackman et al. "Fabrication of Submicrometer Features on Curved Substrates by Microcontact Printing", Science, vol. 269, 4 Aug. 1995, pp. 664–666.

G.M. Shedd et al. "Combinations of point source electron beams and simple electrostatic lenses: Initial demonstrations of micro–scale lenses", Rev. Sci. Instrum. 64(9), Sep. 1993, pp. 2579–2584.

L.P. Muray et al. "Experimental evaluation of a scanning tunneling microscope–microlens system", J. Vac. Sci. Technol. B 9(6), Nov./Dec. 1991, pp. 2955–2961.

K.Y. Lee. "Evaluation and application of a very high performance chemically amplified resist for electron–beam lithography", J. Vac. Sci. Technol. B 11(6) Nov./Dec. 1993, pp. 2807–2811.

*Primary Examiner*—William Powell
*Attorney, Agent, or Firm*—Stephen C. Kaufman

[57] ABSTRACT

A method for microscopical observation of an amorphous specimen. The method comprises the steps of providing a substrate having at least one outer surface that defines an optically flat and predetermined geometric configuration, including at least one discontinuity; disposing an amorphous specimen in contact with the discontinuity of the substrate; and, selecting a virtual focus point which can act as a referent point on a defocus position axis, thereby maximizing the phase-contrast of the specimen.

10 Claims, 6 Drawing Sheets

SUBSTRATE AND METHOD FOR MICROSCOPICAL OBSERVATION OF AMORPHOUS SPECIMENS

FIELD OF THE INVENTION

This invention relates to a substrate and method suitable for optimizing microscopical observation of amorphous specimens, e.g., vitrified specimens.

INTRODUCTION TO THE INVENTION

Cryo-electron microscopical observation, especially of biological specimens, is a known and increasingly important technology. Basic instruction and background reference on this technology may be found in "Low temperature electron microscopy" by Dubochet et al., Ann. Rev. Biophys. Bioeng., vol. 10, 133–149, 1981 or "Electron Microscopy of frozen, hydrated biological specimens" by W. Chiu, Ann. Rev. Biophys. Chem., vol. 15, p. 237–57, 1986 and references therein.

SUMMARY OF THE INVENTION

One aspect of our work in this technology centers on a situation where the dimensions of a specimen of interest may be at a resolution limit of an electron microscope. Here, imaging parameters may be effected by an interplay of at least three disparate characteristics, including specimen characteristics, specimen substrate or support characteristics, and instrument characteristics.

In particular, our work includes as one objective to define a methodology and develop a substrate support for optimizing imaging parameters. To this end, we have discerned that optimization may include an effective balancing of the three cited disparate characteristics (specimen, substrate support, instrument). This point is now highlighted by first setting in apposition an important and typical, if limited, prior art approach to electron-micioscopical observation of vitrified specimens.

Figure 1:
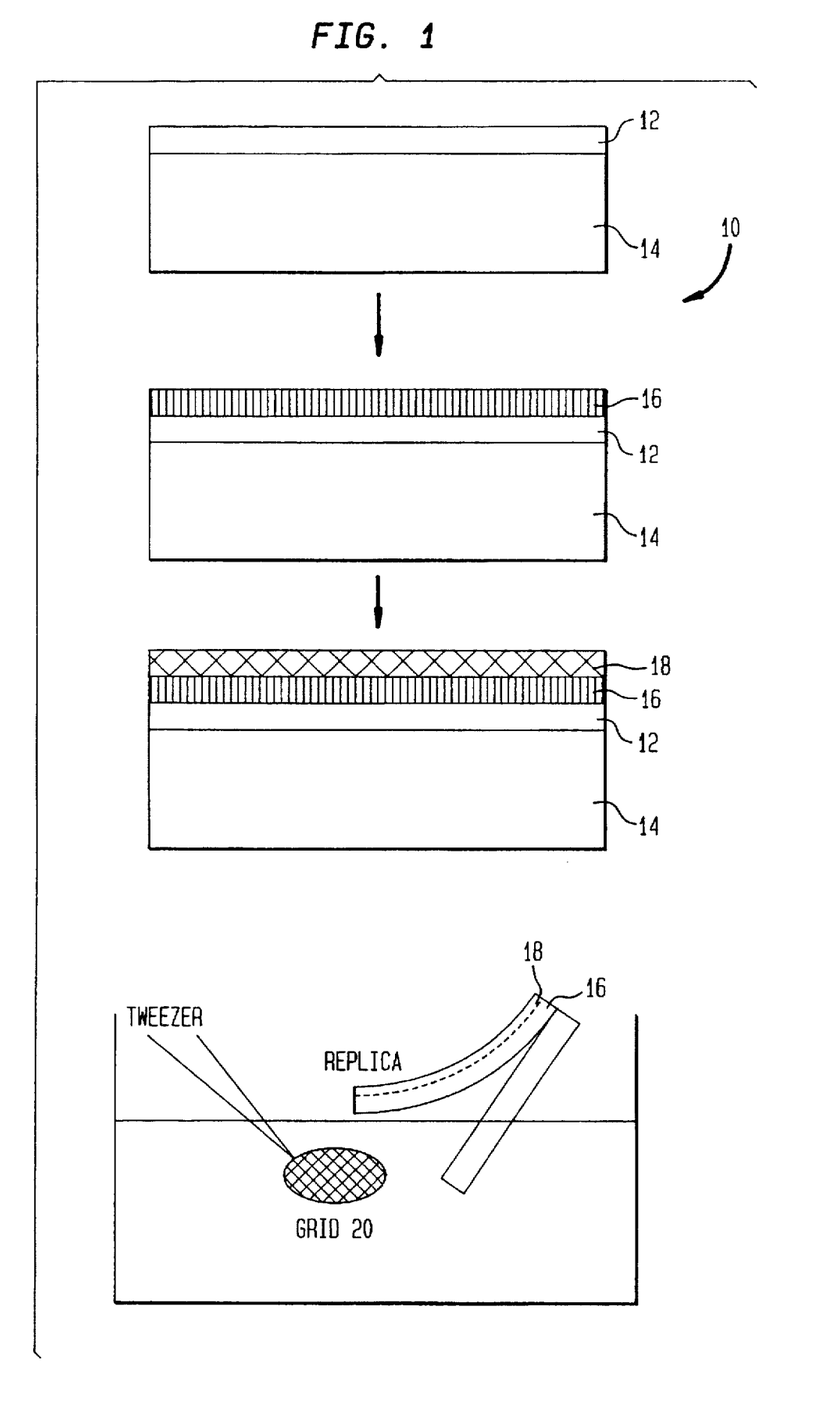
FIG. 1 is an illustration of substrate preparation based upon the prior art.
Figure 2:
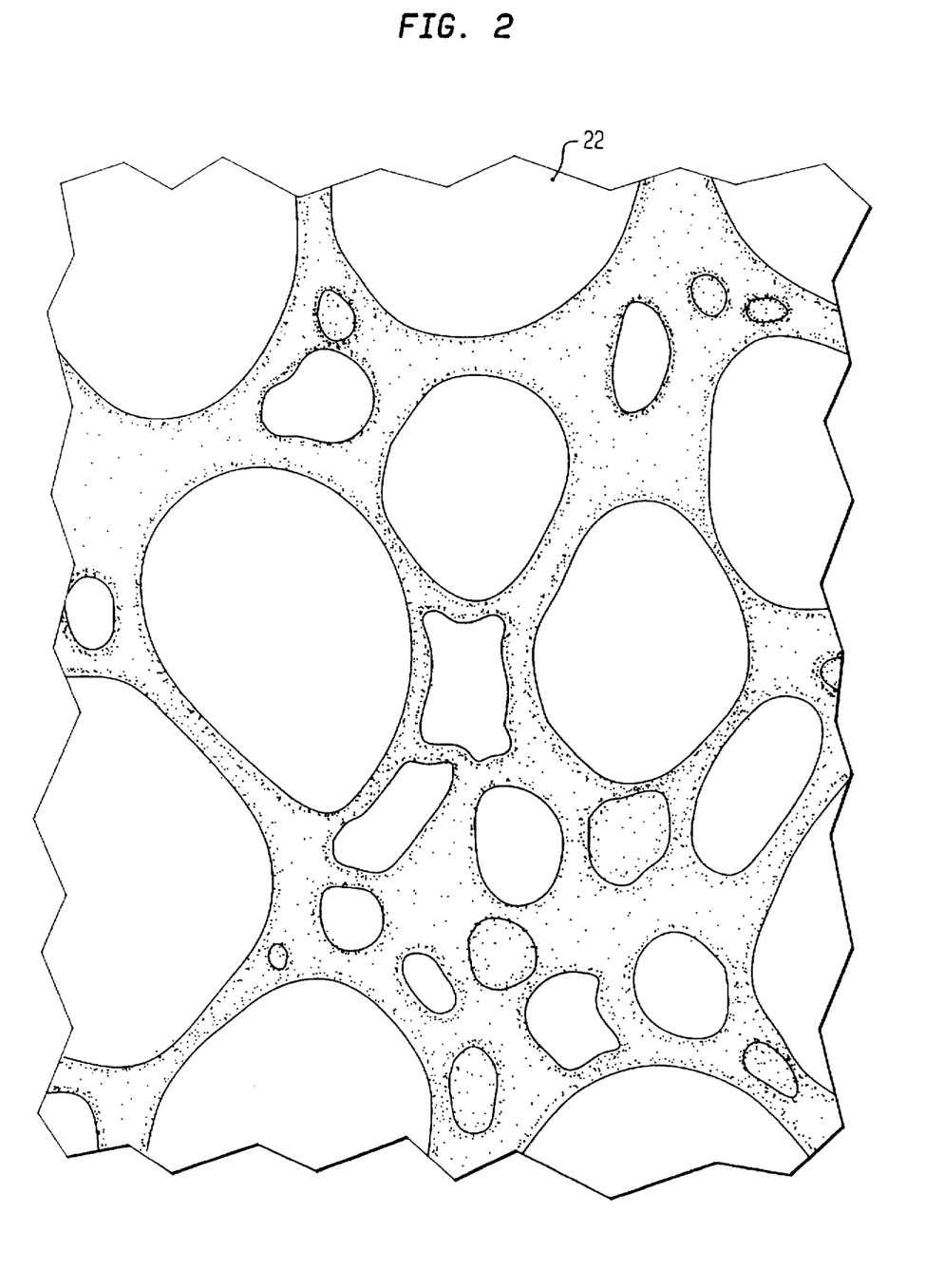
FIG. 2 is a scanning electron micrograph of a self-perforated micro-plastic grid as it is fabricated in the prior art.

FIGS. 1 and 2 show one illustrative approach. FIG. 1 shows that a substrate element 10 may be used to contain and support a specimen, for its subsequent electron-microscopical observation. In general, a typical preparation technique comprises fabrication of the substrate element 10 by spinning a diluted plastic solution 12 (e.g., 0.1–0.4% PMMA, pioloform in ethylacetate) over a humid glass cover slide 14. The plastic film is then coated with a thick carbon layer 16, and a second layer 18 of evaporated gold. Most of the plastic is dissolved, and the metallic replica is transferred to an uncoated electron microscope grid 20.

We note that in this conventional substrate preparation, the final geometries and sizes of the holes cannot be defined exactly, as shown in FIG. 2, numeral 22. In particular, the multi-steps preparation of the film cannot uniquely distribute accurate and well-defined holes over a pattern area. From this situation, in turn, there can arise a problem of defining viable optical imaging parameters, including forming an optimal imaging beam, so as not to preclude high resolution imaging. We now investigate the nature of this problem by directing attention to FIGS. 3, 4.

Figures 3, 4A, 4B:
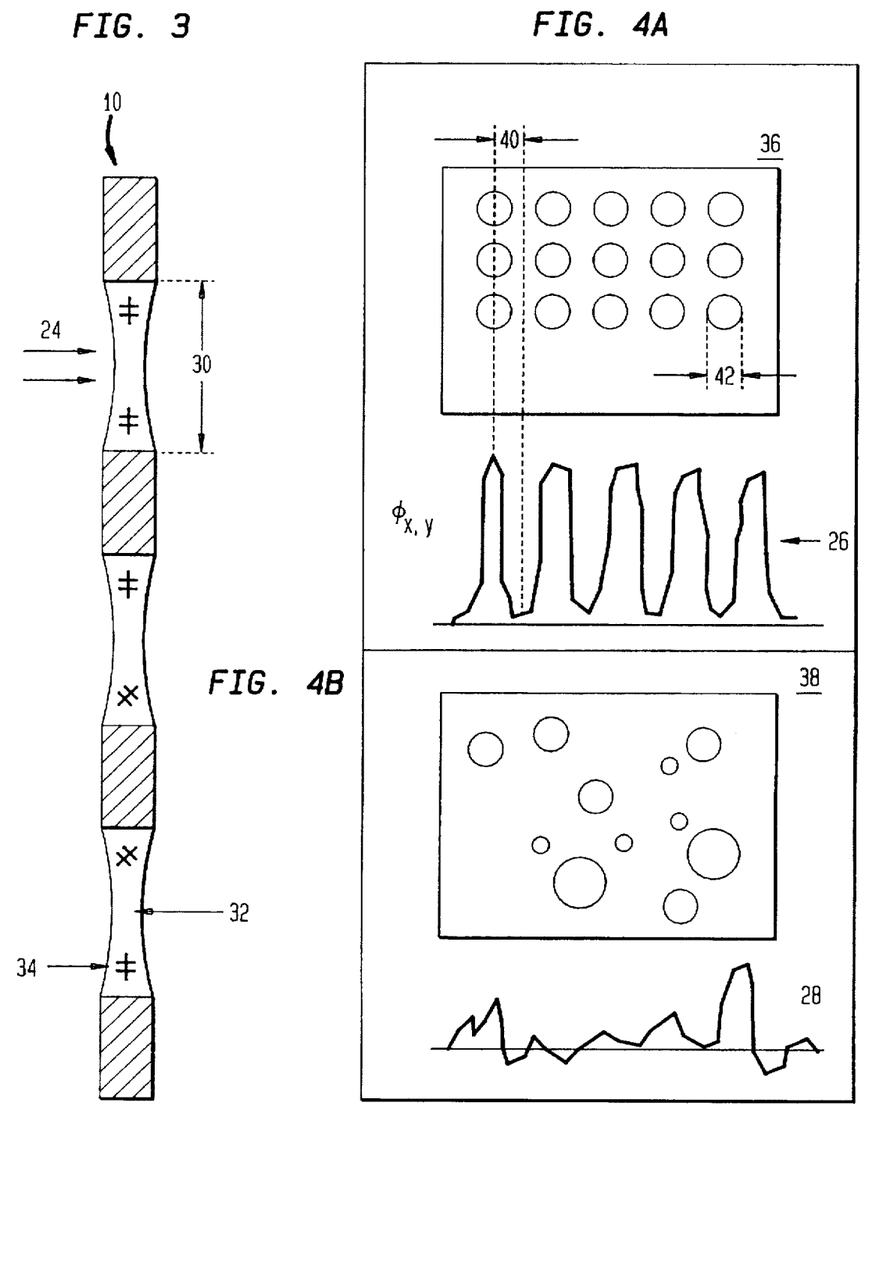
FIG. 3 is a diagrammatic sectional view of a substrate for carrying out the method in accordance with the invention.
FIGS. 4a–b are a diagrammatic top view of the substrate previously shown in FIG. 3 and FIG. 2, respectively, and graphically shows the corresponding illustrative phase contrast functions.

FIG. 3 shows a side view of a FIG. 1 substrate element 10, and a radiation beam 24. Focusing considerations of the incident radiation include the following points.

First, it is preferred to use a thin specimen, in order to minimize instrumental defects such as chromatic and spherical aberrations. However, thin specimens act almost as pure phase objects; therefore, secondly, the production of contrast is produced by defocusing, when operating in a dark-field imaging mode.

Third, with a FIG. 2 type specimen support geometry, a choice of a viable defocus is arbitrary, and in practice, depends on a clearly defined reference point (FIG. 5 "RP"), from which the defocus can be measured. In practice, the reference point is commonly taken to be a point of an edge of a hole of the perforated supporting film. This edge reference point is viable, if not optimal, in the sense that it can avoid burning the specimen, yet defining a defocus condition for an interpretable resolution. Further, the image intensity fluctuation from an average value is proportional to the square root of the number of atoms present, so that the average intensity is roughly proportional to a first power of the projected density of atoms. In sum, it appears that a proper interpretation of high resolution images of amorphous specimen is strongly dependent on a variation of image contrast with defocus, for which a well-defined reference point has to be clearly chosen and configured.

We have now discovered a novel method suitable for microscopical observation of an amorphous specimen contained within a liquid suspension. The novel method encompasses simulating a virtual focusing point that can maximize the phase contrast of the specimen at a controlled energy. This capability, we note, may be advantageously contrasted to the prior art situation discussed above. To this end, the novel method preferably uses a novel substrate for locating and positioning a specimen for electron microscopical observation.

The novel method comprises the steps of:

1) providing a substrate having at least one outer surface that defines an optically flat and predetermined geometric configuration including at least one discontinuity;

2) disposing an amorphous specimen in contact with the discontinuity of the substrate; and 3) selecting a virtual focus point which can act as a reference point on a defocus position axis, thereby maximizing the phase-contrast of the specimen.

The novel substrate of the present invention comprises a wafer having at least one outer surface that is optically flat and comprises a predetermined geometric pattern.

BRIEF DESCRIPTION OF THE DRAWINGS

The invention is illustrated in the accompanying drawings, in which.

DETAILED DESCRIPTION OF THE INVENTION

In this section, we first outline some of the concepts of specimen preparation, image formation and electron wave optics, preferably used to illustrate imaging in an electron microscope.

In high-resolution imaging with an electron microscope, the damage that may be caused during specimen preparation and irradiation by the electron beam may be a limiting factor for resolving the specimen ultrastructure. Cryoelectron microscopy has emerged as a possible technique to overcome this limitation. As a beam has less damaging effect on cooled specimens, due to several mechanisms of cryostabilisation ("Low Temperature Electron Microscopy" by Dubochet et al., Ann. Rev. Biophys. Bioeng., vol. 10, 133–149, 1981) such as the reduction in atomic and molecular diffusion at low temperature, suppression of mass loss and contamination, clearly, a viable method of specimen preparation ("Electron Microscopy of Frozen, Hydrated Biological Specimens" by W. Chiu, Ann. Rev. Biophys. Chem. 1986, vol. 15, pp. 237–257) is to observe the specimen in an aqueous environment. At the same time, however, the damaging effect of ice crystal formation during freezing requires a development of more sophisticated techniques to prevent a freezing artifact. In practice, the preparation can be achieved by freezing the specimen as a thin layer in a suspension on a support film. By using fast freezing rates for quench-freezing in liquid propane/butane cooling fluid, specimens can be adequately prepared for structural preservation, to a high resolution ("Cryo-electron microscopy of viruses" by Adrian et al, Nature, vol. 308, Mar. 1, 1983, pp. 32–36).

Current specimen supporting methods for high-resolution observation are already well known, and they require the formation of ultra-fine holes, typically of 0.05–1.5 micron in diameter, in order to improve the resolving power of the microscope. This has been achieved by using the micro-grid techniques developed by Fukami & Adachi, "Micro Grid Techniques (continued) and Their Contribution to Specimen Preparation Techniques for High Resolution Work", Journal of Electron Microscopy, vol. 21, no. 2, 1972, pp. 99–108. Amorphous specimen such as vitrified biomolecules to be observed in an electron microscope (e.g., a transmission electron microscope or TEM) are typically mounted on a thin, electron transparent polymer membrane or a self-perforated micro-plastic grid rendered conductive with evaporated carbon or gold.

In prior art preparation methods, small water droplets are formed on the surface of a hydrophobic pre-treated glass slide, for example, by using a thin layer of water-repellent (e.g., cation surface active agent). The control of the wetting properties of the glass substrate, by using various mixtures of water-repellents with different hydrophobic properties, permits one to make a micro-grid with hole size within the extent of 0.2–10 micron. By cooling the surface glass below the dew point, e.g., −5 C, and by breathing upon it for making dew drops, the glass slide is immersed in liquid nitrogen for 1–2 seconds, so that the drops are quickly frozen. Next, a plastic material (e.g., cellulose derivatives, 0.5% ethylene dichloride solution of polyvinyl formal or Formvar) is spread on the surface of the glass slide and left until the solvent volatilizes. Then, the glass surface is immersed in a re-hydrophilic agent to allow the plastic film separation from the glass. After washing in water, the plastic film is floated off onto the water surface and transferred to a metallic grid. Then vacuum evaporation of carbon (e.g., 20 nm) and/or gold (e.g., 10 nm) is deposited onto the microgrid layer to reinforce it.

Another, somewhat similar, method is to prepare metal or carbon grids based on the plastic micro grids after electroplating of silver or copper and removing the plastic by dissolution in a solvent.

A major disadvantage of these methods is that the control of hole size, their distribution and the surface quality of the membrane are difficult to control. Thus, in the case of the high resolution microscopical examination of amorphous specimens, and more especially with vitrified biomolecules, a region of the hole which contains an object of interest must be selected as a reference focusing point, and this can be difficult due to undefined geometries and rough surfaces of the hole edge.

Typically, for dark-field imaging, the variation of image contrast with defocus is important for high-resolution because the modifications of magnitude and phase of the waves can create an image. For example, by going out of focus in either direction, the contrast is increased of opposite sign for overfocus and underfocus. However, it is necessary to have some clearly defined reference point from which the defocus can be measured.

This invention is particularly directed to that of providing a substrate whose geometrical properties can give a more sharply defined focal position, compared to the conventional Fresnel fringes for lower resolution work. In practice, phase contrast imaging may be performed by recording at least a series of sub-images in different planes with defocus values which differ slightly. This method can maximize the phase contrast transfer function and minimize the beam-induced drift of the specimen (see Dubochet, supra).

As it will be illustrated in more detail below in a diagram of the different steps involved in the examination of vitrified specimens, the imaging process preferably comprises the selection of an area to be recorded and an adjacent area for focusing, preferably the edge of a hole of a supporting membrane. In all the supporting membranes and processes described in the prior art, the "critical dimensions" of the holes can not be addressed in a controlled and predetermined way. It is an object of the invention to provide a method that enables accurate, reproducible examination of an amorphous specimen used for resolution enhancement equal to the intrinsically present image information resolution.

The "critical dimensions" referred to above include a process of creating a well-defined pattern on a substrate with accurate geometries, typically a periodic arrangement of thin circular holes. Accordingly, a supporting substrate suitable for this arrangement generally comprises silicon and other materials which can be modified by micromachining, etching techniques or any other manufacturing method, thereby enabling the integration of at least a microscopic pattern on the substrate. Thus, an amorphous specimen particle suspension (e.g., molecule, protein, nucleic acid or virus) can be brought in contact with the substrate so as to be interrogated by electromagnetic radiation, in view of its location and identification at high spatial resolution. To some extent, the substrate of the present invention may be used as a convenient minimum-contrast indicator for a well-defined defocus referent point, and therefore provides a unique guide to optimum-defocus positions.

A further advantage of the invention is that the instrumental response characterized by the amplitude contrast transfer function ($-2\cos \gamma$) and the phase contrast transfer function ($-2\sin \gamma$) can be minimized or maximized, respectively. The general object wave function for a weak specimen is defined by an image wave $\psi(x_1,y_1,z_1)$, at the image plane $z=z_1$ modulated by the contributions of specimen and optical system. In phase-contrast imaging, the image is formed by the phase shift between the diffracted wave $\psi(x_b,y_b,z_b)$ and the undiffracted wave $\psi(x_0,y_0,z_0)$. The overall phase shift relies on a component introduced by the specimen itself and a component due to the optical system, typically defocus and spherical aberration. The phase shift $\gamma$ can be expressed by a complex equation, in the case of spherical aberration $C_s$ and a defocus $\delta f$:

$$\gamma = 2\frac{\pi}{\lambda} \left\{ \frac{1}{4} C_s A^2 - \frac{1}{2} \delta f A \right\} \quad [1]$$

where $\delta f$, $C_s$ are defocus and spherical aberration respectively.

It has been demonstrated that for different values of defocus, the transfer functions reach their zeros and extrema at some characteristic value of angular aperture ("Three dimensional algebraic reconstruction from three mutually orthogonal projections" by Ximen et al, Optik 71, No. 4 (1985), pp. 145–148). This is shown in FIG. 4, functions 26 and 28, illustrating the enhancement provided by the invention versus the prior art, respectively. Because of the desirable high resolution work, and because of the number of images per measurement, focus drift and object drift can appear. To this end, the method of the invention may be characterized in that the value of the oscillating transfer functions can be accurately controlled over the entire defocusing range by virtually defining a referent focusing point which, for example, allows one to pass through the total focus interval in both directions. Nevertheless, processing in the reverse order has to be carefully controlled in particular experiments with very sensitive materials, because it may cause beam damage or affect the high resolution information.

Attention is now directed once again to FIG. 3. The substrate element 10 shown in FIG. 3 comprises a discontinuity e.g., an aperture 30, in which an amorphous thin film 32, e.g., a vitrified liquid film of typically an aqueous solution (though any suitable solvent, physiological or similar buffers can be used), can be associated within the discontinuity 30. A specimen 34 is suspended in the thin film 32 in view of its interrogation with said radiation, e.g., the electromagnetic wave 24.

The applied energy used in the invention is any form of electromagnetic radiation, and in FIG. 1 to 7 this electromagnetic energy is an electron beam.

The substrate element 10 comprises a transparent or opaque, conductive or semi-conductive material (e.g., silicon) or mixture of materials (e.g., GaAs, silicides), on at least one face of which some material is removed in a process evolving to a one-sided or two-sided shaped discontinuity or aperture 30. The substrate element 10 may have any suitable thickness, typically of the order of 1–2 micron.

At least one aperture is formed, by any known method, in or through the substrate material. In the case of a partial opening in the latter, the resulting membrane on one of the faces has to be thin enough to be at least partly transparent to the incident radiation, so that some radiation can pass through it. In the practice of the invention, apertures in the range of about 0.01–10 micron in diameter are preferred.

It is noted that the fabrication of such a substrate element 10 may be processed, for example, via dry etching technologies or wet chemical etching methods used in the semi-conductor industry.

Considering the fabrication by partial opening in the material, the use of scanning probe techniques for atomic or molecular manipulations can be practiced in accordance with the method of the invention. The nanostructure fabrication techniques using field evaporation and local heating in scanning probe microscope such as the STM, AFM and SNOM have been demonstrated for making atomic patterns on metallic surfaces ("Nanoscale layer removal of metal surfaces by scanning probe microscope scratching" by Sumomogi et al, J. Vac. Sci. Technol. B., Vol. 13, No. 3, May/June 1995, pp. 1257–1260 and "Fabrication of nanostructures using scanning probe microscopes" by Hosaka et al, J. Vac. Sci. Technol. B 13(6), November/December 1995, pp. 2813–2818), or on single-crystal silicon, oxide and nitride by direct writing, or by using amorphous silicon as a resist ("Atomic force microscope lithograph using amorphous silicon as a resist and advances in parallel operation" by Minne et al, J. Vac. Sci. Technol. B 13 (3), May/June 1995, pp. 1380–1385).

Another important microlithography method involves molecular contact printing ("Fabrication of Submicrometer Features on Curved Substrates by Microcontact Printing" by Jackman et al, Science, Vol. 269, 4 Aug. 1995, pp. 664–666). An elastomeric stamp, formed by replication of an electron-beam ruled master, makes conformal contact with the substrate on a molecular scale and transfers to it the resist. It can be used for direct processing by contact and for direct patterned transfer of organic and inorganic materials. The referenced publication by Jackman and Whitesides describes that this method enables the fabrication of gold microstructures patterned on various surfaces.

A preferred version of the method in accordance with the invention is characterized in that the substrate element 10 may have a number of apertures 30, all preferably of similar shapes and sizes (e.g., circular holes), and preferably arranged in periodic patterns. In order to achieve the preferred, configuration of FIG. 4a substrate 36, versus FIG. 4b substrate 38 of the prior art, a focused ion beam and reactive-ion etching are preferably used to create a hole. This technique for creating such a patterned substrate 36 has the advantage that no masking or lithography is required, and that holes through different layers (e.g., oxide/silicon/oxide) can be self-aligned.

The concept of making micron scale lenses and apertures has been disclosed in a number of papers and patents, such as in the following: U.S. Pat. No. 5,122,663 to Chang, "Combinations of point source electron beams and simple electrostatic lenses: Initial demonstrations of micron-scale lenses" by Shedd et al., Rev. Sci. Instrum., vol 64(9), pp 2579–2584, 1993, "Experimental evaluation of a scanning tunneling microscope-mictolens system" by Muray et al., J. Vac. Sci. Technol., vol B(9), pp 2955–2961, 1991 which disclosures are incorporated by reference herein.

Figure 7:
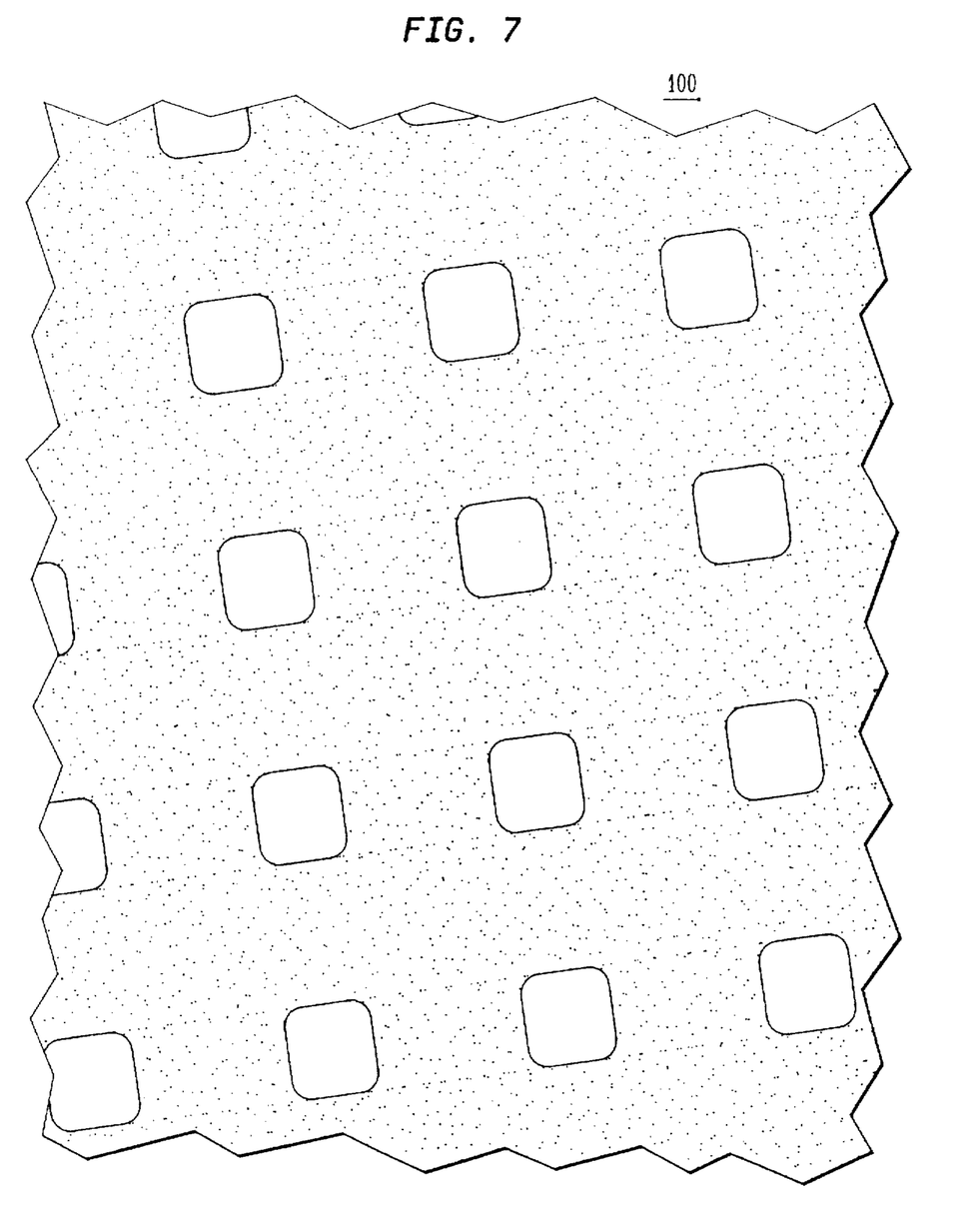
FIG. 7 is a transmission electron micrograph of a periodic hole pattern micro-fabricated in a substrate according to the invention.

This invention therefore preferably uses a microfabrication process, preferably derived from the background work published by Lee et al., "Evaluation and application of a very high performance chemically amplified resist for electron-beam lithography", J. Vc. Sci. Technol., vol. B11 (6), 2807–2811 1993 and incorporated by reference herein. For the purpose of the present method, modifications of the process described above have been performed. The periodic pattern of about 1 micron-diam., shown in FIG. 7, is made from 1–2 micron thick silicon membrane formed by wet isotropic etching (see U.S. Pat. No. 4,919,749 to Mauger), and supported on a 500 micro- thick two-sided polished wafer.

After cleaning the wafer by a conventional procedure in a mixture of sulfuric acid and peroxide, priming and coating with a 1 micron-thick electron beam positive tone chemically amplified resist (e.g., KRS), which provid high aspect ratio patterning and high RIE resistance, the resist is baked, for example at 110 C, 5 minutes, before electron-beam exposure at about 50 kV using a dose of about 30 microC/cm$^2$. The wafer preferably is patterned with 1-5 micron circles. After exposure, the wafer is developed in typically 0.15N tetramethyl ammonium hydroxide for about 90 s. The wafer is then preferably reactive ion etched, for example, in SF$_6$/CBrF$_3$ under primary vacuum (e.g., 10$^{-2}$ Torr) at an etch rate in the range of 0.01–0.1 micron/min.

As it has been reported in Lee et al., such a resist yields to high etch selectivity to obtain etched holes through the silicon membrane from the masked surface. In order to create the holes through the silicon with very vertical etched profiles, additional etching on the back surface of the silicon is processed. This defines the critical dimensions 40 and 42, as it is illustrated in FIGS. 4a. The remaining resist preferably is stripped in typically hot n-methyl pyrrolidinone followed by oxygen ashing, cleaning as mentioned above, and then etching in buffered HF. The resulting hole-pattern may be sealed by anodic bonding at low-temperature (300–600 C) to a glass or Pyrex substrate of typically 3×3 mm compatible with conventional TEM-holder, in which a hole of about 0.3–1 mm-diam may be sonically drilled through. Note that a direct use of the patterned membrane may be possible, but bonding to a glass substrate is preferred for mechanical stability.

Figure 5:
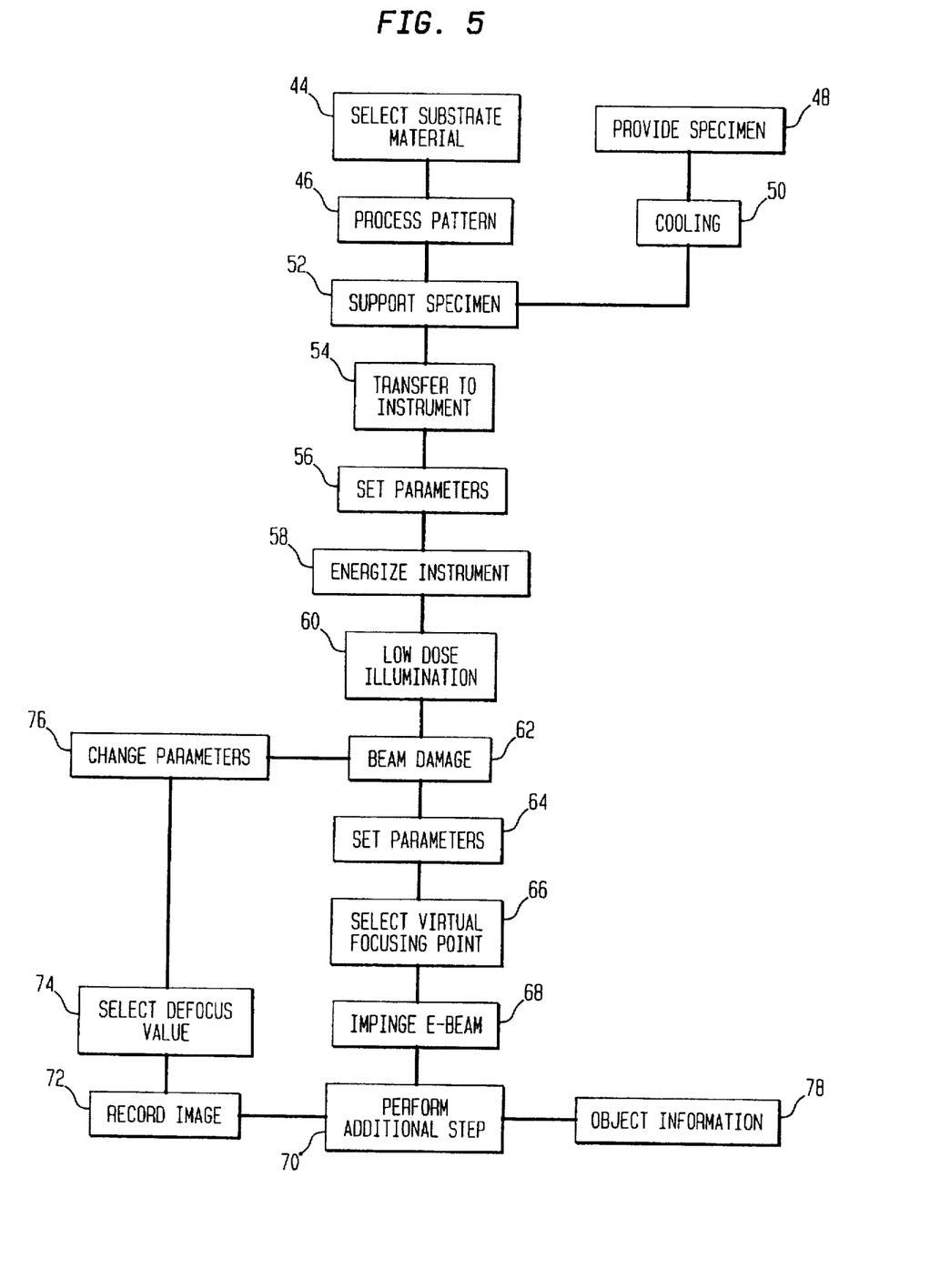
FIG. 5 is an illustrative flowchart of a method of the present invention.

Attention is now directed to FIG. 5, which illustrates how to realize the present method in view of obtaining specimen information, for example, by creating a high-resolution image. The procedure which has been chosen is illustrative of the method used with one illustrative embodiment, and it may be adapted or modified to match the specificities of specimens and applications of those skilled in the art.

A preferred version of the present method is characterized in that, for determining preferably high-resolution information of an amorphous specimen, it is suitable to use a substrate element supporting the latter having at least a surface pattern optically flat. The surface pattern preferably has properties (e.g., geometries, nature) which can optimize the selection of a virtual defocus referent point on the axis of optimum defocus positions, resulting in the formation of a series of sub-images. This process comprises a selection (44) of a substrate material compatible with the specimen and imaging parameters. For example, a silicon wafer double sided polished is processed, and a pre-determined pattern is fabricated (46). According to one aspect of the invention, a specimen in suspension in a solution (48) is rapidly frozen by using a cooling mixture (50) (see detailed description above) and brought into proximity of the substrate element, typically moving into the discontinuities or apertures of the pattern (52).

The resulting assembly substrate-specimen is transferred into typically an electron microscope (54) by avoiding any drastic temperature gradient changes. After thermal stabilization of the system, parameters for the microscopical examination of the specimen are set (56), and the lenses ae energized (58) by a current.

A first examination at low dose (60) may be done, and an area of interest may be selected in such a way that beam-induced drift of the specimen or any beam damage (62) is minimized. Then, typically 2 positions of condenser may be selected (64), one place to record, one place to focus.

In general, the invention is directed for selecting a virtual referent focusing point (66) at the edge of one of the apertures of the microfabricated pattern. After defining this position, the microscope may be operated in dark-field phase contrast mode (68) of imaging, to subsequently (70) record (72) an image with a defined defocus value (74).

Then, for example, continuous series of images may be performed at slightly different defocus position (76) on the axis of optimum defocus positions referenced to the initial virtual defocusing point.

By analyzing, for example, images recorded on photographic micrographs, high-resolution information about the specimen can be obtained (78). Using the described method, the maximum point resolution that has been commonly reported in the literature on a test specimen comprising a frozen hydrated specimen of Tobacco Mosaic Virus can be improved by at least a factor 2.

Figure 6A:
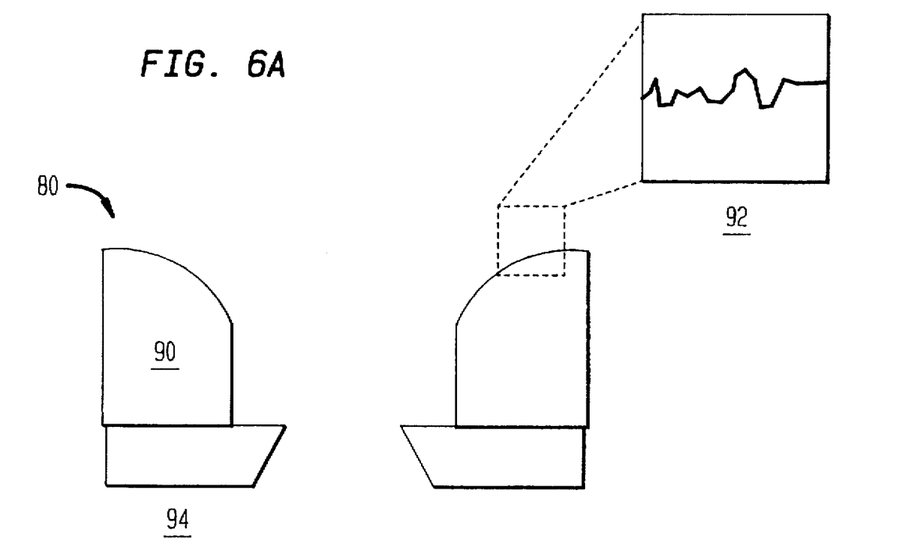
FIGS. 6a–c illustrate schematic cross-sections of a hole fabricated by the prior art techniques, and a hole generated with a method in accordance with the invention.
Figure 6B:
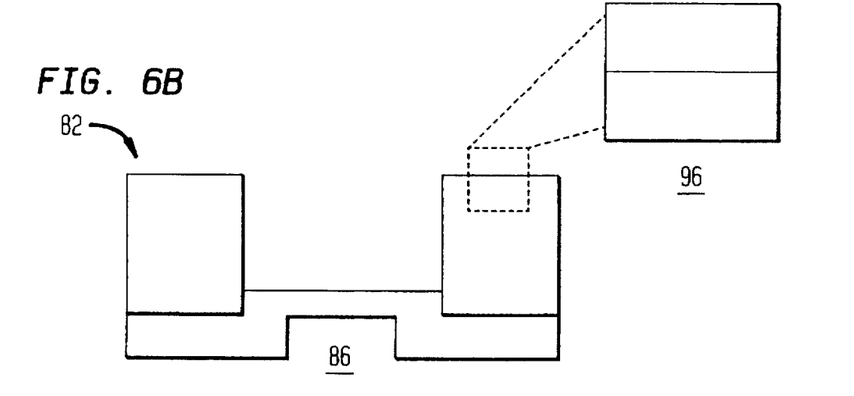
Figure 6C:
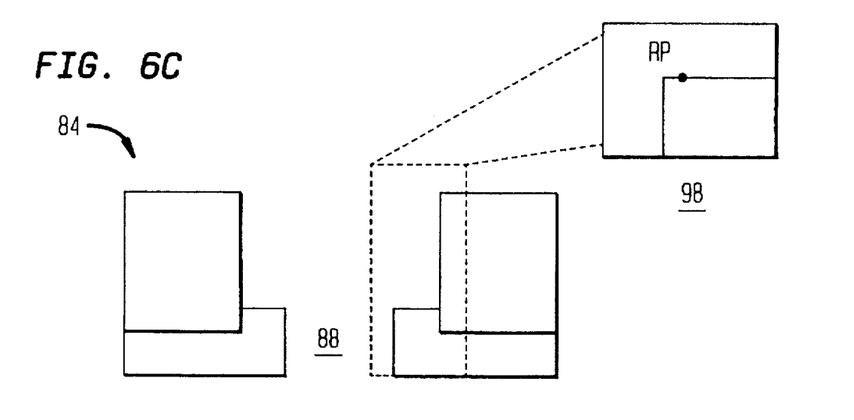

FIGS. 6a–c compare illustrative diagrams of substrates done in the prior art 80, and fabricated by a method in accordance with the invention 82, 84, resulting in a partial opening 86, or in a complete discontinuity or aperture 88. In comparison, the prior art fabrication yields to a perforated membrane 90 having an un-characterized surface profile 92, supported by a conventional electron microscope grid 94. Furthermore, the three-dimensional shape of the object substrate is undefined and unreproducible. The method of this invention, in contrast, allows the fabrication of an integrated pattern (e.g., periodic arrangement of circular holes), having discontinuities 86 or 88 with accurate (e.g., at least 10 nm accuracy) high aspect ratio dimensions, yielding to surface profiles 96, 98, that are optically flat, this thereby provides an inventive guide to optimum defocus positions —RP—, typically located at the edge of at least one of the discontinuities of the substrate. FIG. 7 shows a transmission electron micrograph of a periodic hole pattern 100 microfabricated in a substrate in accordance with the invention.

We claim:

1. A method for microscopical observation of an amorphous specimen, which method comprises the steps of:

(1) providing a substrate having at least one outer surface that defines an optically flat configuration including at least one discontinuity;

(2) disposing an amorphous specimen in contact with the discontinuity of the substrate; and (3) selecting a virtual focus point which can act as a reference point on a defocus position axis, thereby maximizing the phase-contrast of the specimen.

2. A method according to claim 1, including providing a substrate comprising silicon wafer.

3. A method according to claim 1, comprising a step of micromachining the substrate by etching techniques.

4. A method according to claim 3, comprising using an anodic dissolution method.

5. A method according to claim 1, comprising a step of defining a geometric configuration with geometries having dimensions below the diffraction limit.

6. A method according to claim 1, wherein the discontinuity defines an aperture.

7. A method according to claim 1, comprising arranging the discontinuities in a periodic pattern.

8. A method according to claim 1, comprising a step of using a focused ion beam for generating the geometric configuration.

9. A method according to claim 1, comprising disposing a vitrified specimen within the discontinuity.

10. A method according to claim 1, comprising selecting the virtual focus point by an automated process.

* * * * *